United States Patent
Hidaka et al.

(10) Patent No.: US 10,870,084 B2
(45) Date of Patent: Dec. 22, 2020

(54) WATER-ALCOHOL SEPARATION SYSTEM AND WATER-ALCOHOL SEPARATION METHOD FOR PRODUCING ALCOHOL

(71) Applicant: Mitsubishi Chemical Corporation, Chiyoda-ku (JP)

(72) Inventors: Hideto Hidaka, Chiyoda-ku (JP); Yohei Sato, Chiyoda-ku (JP)

(73) Assignee: Mitsubishi Chemical Corporation, Chiyoda-ku (JP)

( * ) Notice: Subject to any disclaimer, the term of this patent is extended or adjusted under 35 U.S.C. 154(b) by 0 days.

(21) Appl. No.: 16/571,362

(22) Filed: Sep. 16, 2019

(65) Prior Publication Data
US 2020/0009507 A1 Jan. 9, 2020

Related U.S. Application Data

(63) Continuation of application No. PCT/JP2018/010109, filed on Mar. 15, 2018.

(30) Foreign Application Priority Data

Mar. 17, 2017 (JP) .................. 2017-053578

(51) Int. Cl.
*B01D 61/36* (2006.01)
*B01D 69/10* (2006.01)
(Continued)

(52) U.S. Cl.
CPC ......... *B01D 61/366* (2013.01); *B01D 61/362* (2013.01); *B01D 61/368* (2013.01);
(Continued)

(58) Field of Classification Search
CPC .. B01D 61/366; B01D 61/362; B01D 61/368; B01D 69/10; B01D 71/028; C02F 11/448; C07C 29/78
(Continued)

(56) References Cited

U.S. PATENT DOCUMENTS

2010/0206789 A1 8/2010 Yukumoto et al.

FOREIGN PATENT DOCUMENTS

JP 63-162002 A 7/1988
JP 63162002 A * 7/1988
(Continued)

OTHER PUBLICATIONS

English translation of the International Preliminary Report on Patentability dated Sep. 17, 2019 in PCT/JP2018/010109 filed Mar. 15, 2018, 8 pages.

(Continued)

*Primary Examiner* — Deborah D Carr
(74) *Attorney, Agent, or Firm* — Oblon, McClelland, Maier & Neustadt, L.L.P.

(57) ABSTRACT

The invention provides a water-alcohol separation system and a method for water-alcohol separation for producing a high purity alcohol while achieving energy saving as the whole process. Namely, a water-alcohol separation system including plural separation membrane modules connected in series, a vacuum apparatus for reducing a pressure at a permeated side of each of the separation membrane modules, and a condenser for condensing a vapor that has passed through a membrane, in which plural independent vacuum systems reduce the pressure at the permeated side of the membrane of the separation membrane modules.

12 Claims, 5 Drawing Sheets

(51) Int. Cl.
  *B01D 7/02* (2006.01)
  *C02F 1/44* (2006.01)
  *C07C 29/78* (2006.01)
  *C02F 101/34* (2006.01)
  *B01D 71/02* (2006.01)

(52) U.S. Cl.
  CPC .......... *B01D 69/10* (2013.01); *B01D 71/028* (2013.01); *C02F 1/448* (2013.01); *C07C 29/78* (2013.01); *B01D 2311/06* (2013.01); *B01D 2317/025* (2013.01); *C02F 2101/34* (2013.01)

(58) Field of Classification Search
  USPC ......................................................... 568/992
  See application file for complete search history.

(56) References Cited

FOREIGN PATENT DOCUMENTS

| | | | |
|---|---|---|---|
| JP | 05-000226 A | 1/1993 | |
| JP | 05-103956 A | 4/1993 | |
| JP | 2000-334257 A | 12/2000 | |
| JP | 2005-177535 A | 7/2005 | |
| JP | 2005177535 A * | 7/2005 | |
| JP | 2008-086988 A | 4/2008 | |
| JP | 2009-165994 A | 7/2009 | |
| JP | 2009165994 A * | 7/2009 | ............ B01D 61/58 |
| JP | 2013-240795 A | 12/2013 | |
| JP | 2013240795 A * | 12/2013 | |
| JP | 2014-118377 A | 6/2014 | |

OTHER PUBLICATIONS

International Search Report dated Jun. 19, 2018 in PCT/JP2018/010109 filed Mar. 15, 2018.

* cited by examiner

WATER-ALCOHOL SEPARATION SYSTEM AND WATER-ALCOHOL SEPARATION METHOD FOR PRODUCING ALCOHOL

CROSS-REFERENCE TO RELATED APPLICATION

This is a continuation of International Application No. PCT/JP2018/010109, filed on Mar. 15, 2018, and designated the U.S., and claims priority from Japanese Patent Application No. 2017-053578 which was filed on Mar. 17, 2017, the entire contents of which are incorporated herein by reference.

TECHNICAL FIELD

The present invention relates to a water-alcohol separation system and a method for water-alcohol separation for producing an alcohol; and especially to a water-alcohol separation system and a method for water-alcohol separation for producing a high purity alcohol achieving energy saving as the whole process.

BACKGROUND ART

It is difficult to obtain a high purity organic compound solely by ordinary rectification by removing only water from a mixture of water and an organic compound, such as an alcohol, a ketone, and an ether, because the mixture of water and an organic compound forms an azeotropic mixture which has a minimum boiling point.

Therefore, as a method for recovering only an organic compound with high purity from the mixture of an organic compound and water, a method in which most of the water is removed by distillation, and then the remaining water is removed by a pressure swing adsorption apparatus (hereinafter also abbreviated as "PSA") using an adsorbent, has been proposed (see Patent Document 1).

Also, as a method for dehydrating a mixture of an organic compound and water without increasing the size of apparatus, a method in which a membrane separation means is placed between a distillation column and a PSA has been proposed. In addition, a method in which a purge gas discharged from a PSA is supplied to a membrane separation means to yield a high purity organic compound has been proposed (see Patent Document 2).

Furthermore, a method for producing an organic compound, in which a mixture of water and an organic compound containing water desorbed from a PSA is fed to a membrane separation apparatus equipped with a specific zeolite membrane, so that the efficiency as the whole process is high, has been reported (see Patent Document 3).

CITATION LIST

Patent Document

[Patent Document 1] Japanese Patent Laid-Open No. 2000-334257
[Patent Document 2] Japanese Patent Laid-Open No. 2008-86988
[Patent Document 3] Japanese Patent Laid-Open No. 2014-118377

SUMMARY OF INVENTION

A PSA used in Patent Document 1 or 2 requires increase in its size in order to improve its performance (to increase the alcohol concentration), or tolerate decrease in the recovery rate of an alcohol due to a regeneration operation in return for performance improvement. Meanwhile, in the case of a membrane separation apparatus used in Patent Document 3, it is enough to connect a plurality of membrane separation apparatus in series in order to enhance its performance.

On the other hand, when a plurality of membrane separation apparatuses are connected in series, the alcohol concentration increases toward the downstream side of the process, so it becomes necessary to reduce the pressure and attain a higher degree of vacuum. This requires enormous energy, and there is also a problem that it is necessary to increase the capacity of the pump.

In view of the above, an object of the present invention is to provide a water-alcohol separation system and a method for water-alcohol separation for producing a high purity alcohol while achieving energy saving as the whole process.

The present inventors have conducted various studies in order to attain the above object, and as a result have arrived at an idea of a method in which a plurality of vacuum systems are installed in a water-alcohol separation system where a plurality of separation membrane modules are arranged in series, and by which the energy required for pressure reduction can be decreased. The inventors have further arrive at an idea that the energy required for condensing the vapor having passed through a membrane (permeated component) can be reduced and reduction of the energy consumption as the whole is attainable by installing a plurality of vacuum systems and providing each vacuum system with a condenser for the vapor having passed through a membrane of a separation membrane module (permeated component), which makes it possible to use an energy efficient coolant according to the necessary conditions, in contrast to a case where there is only one vacuum system, and therefore only one coolant usable for condensing the gas separated in a vacuum state to entail inadequate energy efficiency for condensation. The present invention has been accomplished based on such ideas.

That is, the outline of the present invention is as follows.

[1] A water-alcohol separation system comprising:
a plurality of separation membrane modules connected in series,
a vacuum apparatus for reducing the pressure at a permeated side of a membrane of each of the separation membrane modules, and
a condenser for condensing a vapor that has passed through the membrane, wherein:
a plurality of independent vacuum systems which have at least two vacuum apparatus and condensers reduce the pressure at the permeated side of the membrane of each of the separation membrane modules.

[2] The water-alcohol separation system according to [1], wherein:
the plurality of the independent vacuum systems comprise at least a first vacuum system and a second vacuum system, and
a pressure $P_1$ at a vacuum side of a membrane of a separation membrane module placed most downstream in a first membrane module unit depressurized by the first vacuum system is higher than a pressure $P_2$ at a vacuum side of a membrane of a separation membrane module placed most downstream in a second membrane module unit depressurized by the second vacuum system.

[3] The water-alcohol separation system according to [1] or [2], wherein the plurality of the independent vacuum systems comprise at least a first vacuum system and a second vacuum system; the first vacuum system is provided with a first condenser, and the second vacuum system is provided with a second condenser; and a temperature $T_1$ of a coolant retained by the first condenser is higher than a temperature $T_2$ of a coolant retained by the second condenser.

[4] The water-alcohol separation system according to [1] or [2], wherein the plurality of the independent vacuum systems comprise at least a first vacuum system and a second vacuum system; the first vacuum system is provided with a first condenser, and the second vacuum system is provided with a second condenser; and a temperature of a coolant retained by the first condenser is 20° C. or higher, and a temperature of a coolant retained by the second condenser is 35° C. or lower.

[5] The water-alcohol separation system according to [1] or [2], wherein the plurality of the independent vacuum systems comprise at least a first vacuum system and a second vacuum system; the first vacuum system is provided with a first condenser, and the second vacuum system is provided with a second condenser; and a temperature of a coolant retained by the first condenser is 0° C. or higher, and a temperature of a coolant retained by the second condenser is 5° C. or lower.

[6] The water-alcohol separation system according to [1] or [2], wherein the plurality of the independent vacuum systems comprise at least a first vacuum system, a second vacuum system, and a third vacuum system; the first vacuum system is provided with a first condenser, the second vacuum system is provided with a second condenser, and the third vacuum system is provided with a third condenser; and a temperature of a coolant retained by the first condenser is 20° C. or higher, a temperature of a coolant retained by the second condenser is 35° C. or lower, and a temperature of a coolant retained by the third condenser is 5° C. or lower.

[7] The water-alcohol separation system according to any one of [2] to [6], wherein a pressure at a vacuum side of a separation membrane module placed most downstream in a first membrane module unit depressurized by the first vacuum system is 20 kPa (absolute pressure) or less.

[8] The water-alcohol separation system according to any one of [1] to [7], wherein the separation membrane module is provided with an inorganic porous support-zeolite membrane complex comprising a zeolite membrane on the surface of an inorganic porous support.

[9] A method for water-alcohol separation comprising a step of introducing a water-alcohol mixture into a plurality of separation membrane modules connected in series, and a separation step of separating water and an alcohol from each other by controlling a plurality of the separation membrane modules connected in series by a plurality of independent vacuum systems;

wherein the separation step comprises a first separation step of separating the water-alcohol mixture by reducing a pressure of a membrane module by a vacuum system to a pressure $P_1$, and a second separation step of separating the water-alcohol mixture after the first separation step by reducing a pressure of a membrane module by a further vacuum system to a pressure $P_2$;

wherein the pressure $P_1$ of the first separation step, and the pressure $P_2$ of the second separation step are different.

[10] The method for water-alcohol separation according to [9], wherein the plurality of the independent vacuum systems comprise:

a first vacuum system and a second vacuum system; and a first separation step in which the first vacuum system depressurizes a permeated side of a first membrane module unit, and a second separation step in which the second vacuum system depressurizes a permeated side of a second membrane module unit; and a pressure $P_1$ at a vacuum side of a separation membrane module placed most downstream in the first membrane module unit is higher than a pressure $P_2$ at a vacuum side of a separation membrane module placed most downstream in the second membrane module unit.

[11] The method for water-alcohol separation according to [9] or [10] comprising a first condensation step of condensing a vapor that has passed through a membrane and is obtained in the first separation step, and a second condensing step of condensing a vapor that has passed through a membrane and is obtained in the second separation step;

wherein a temperature $T_1$ of a coolant retained by a condenser in the first condensation step is higher than a temperature $T_2$ of a coolant retained by a condenser in the second condensation step.

[12] The method for water-alcohol separation according to [9] or [10], wherein the plurality of the independent vacuum systems comprise at least a first vacuum system and a second vacuum system; the first vacuum system is provided with a first condenser, and the second vacuum system is provided with a second condenser; and a temperature of a coolant retained by the first condenser is 20° C. or higher, and a temperature of a coolant retained by the second condenser is 35° C. or lower.

[13] The method for water-alcohol separation according to [9] or [10], wherein the plurality of the independent vacuum systems comprise at least a first vacuum system and a second vacuum system; the first vacuum system is provided with a first condenser, and the second vacuum system is provided with a second condenser; and a temperature of a coolant retained by the first condenser is 0° C. or higher, and a temperature of a coolant retained by the second condenser is 5° C. or lower.

[14] The method for water-alcohol separation according to [9] or [10], wherein the plurality of the independent vacuum systems comprise at least a first vacuum system, a second vacuum system, and a third vacuum system; the first vacuum system is provided with a first condenser, the second vacuum system is provided with a second condenser, and the third vacuum system is provided with a third condenser; and a temperature of a coolant retained by the first condenser is 20° C. or higher, a temperature of a coolant retained by the second condenser is 35° C. or lower, and a temperature of a coolant retained by the third condenser is 5° C. or lower.

[15] The method for water-alcohol separation according to any one of [10] to [14], wherein a pressure at a vacuum side of a separation membrane module placed most downstream in the first membrane module unit is 20 kPa or less.

[16] The method for water-alcohol separation according to any one of [9] to [15], wherein the separation membrane module is provided with an inorganic porous support-zeolite membrane complex comprising a zeolite membrane on the surface of an inorganic porous support.

In this regard, the method of the above [12] is effective when the concentration of the concentrated alcohol obtained in the separation step is 98% or more, and more preferably 99% or more.

Further, the method of the above [13] or [14] is effective when the concentration of the concentrated alcohol obtained in the separation step is 99% or more, and more preferably 99.8% or more.

According to the present invention, it is possible to provide a water-alcohol separation system, and a method for water-alcohol separation for producing a high purity alcohol while achieving energy saving as the whole process.

DESCRIPTION OF EMBODIMENTS

Figure 1:
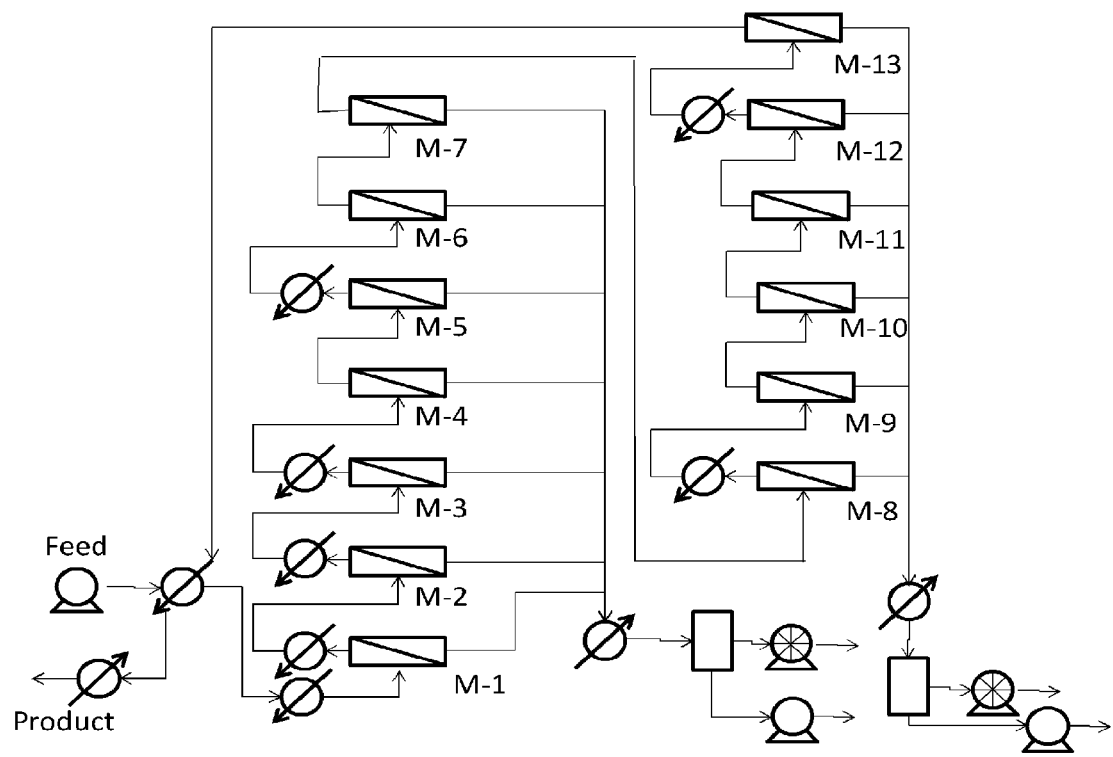
FIG. 1 shows a schematic diagram of a water-alcohol separation system including a first vacuum system and a second vacuum system of an embodiment of the present invention.

The present invention will be described in detail below with reference to embodiments, provided that the present invention be not restricted by embodiments described explicitly or implicitly herein. In addition, each embodiment described herein can be variously modified without departing from the scope of the invention.
1. System for Separating Water and Alcohol A water-alcohol separation system of an embodiment of the present invention may be used favorable in an apparatus for separating water and an alcohol for producing an alcohol.

In general, the method for producing an alcohol has a fermentation step, in which an alcohol fermentation raw material is fermented to yield a water-alcohol mixture, a concentration step, in which the water-alcohol mixture is introduced into a distillation column and concentrated, and a separation step, in which the water-alcohol mixture (liquid or gas) that has undergone the concentration step is introduced into a membrane separation apparatus and the water and alcohol in the mixture are separated.

At dehydration by a membrane (separation step), depressurization at the permeated side is a general technique in order to increase the partial pressure difference of water during permeation. At this time to prevent the permeated component (vapor having permeated the membrane) from being sucked by a vacuum apparatus of the vacuum system, for example, a vacuum pump, it is necessary to chill and condense the permeated component by installing a condenser (heat exchanger) upstream of the vacuum pump such that its vapor pressure becomes lower than the pressure at the permeated side. The heat load (kW) of condensation is represented by the product of the permeated amount of the permeate liquid (permeated component) and the latent heat of condensation. In this regard, the condensation temperature differs depending on the target alcohol concentration (final product). This is because, as the alcohol concentration in a concentrating fluid increases, the water partial pressure in the concentrating fluid decreases, therefore the pressure at the permeated side is required to be lowered to secure the difference in the water partial pressure at the time of permeation. As the pressure at the permeated side is decreased (the degree of vacuum is increased), the condensation temperature required for condensation also decreases. In other words, in a case where there is only one vacuum system, the condensation load needs to be borne by a cold source at a condensation temperature set according to the concentration of the final product.

A water-alcohol separation system of an embodiment of the present invention includes a plurality of separation membrane modules connected in series, a vacuum apparatus for reducing the pressure at the permeated side of the separation membrane modules, and a condenser for condensing a vapor that has passed through a membrane, wherein a plurality of independent vacuum systems reduce the pressure at the permeated side of the separation membrane modules.

That is, in a water-alcohol separation system provided with two or more stages of separation membrane modules (hereinafter, also simply referred to as "membrane modules") connected in series, a plurality of independent vacuum systems have at least two vacuum apparatus and condensers, so that membrane dehydration at different pressures at the permeated sides becomes possible. Namely, since in the case of a concentrating fluid fed to an upstream membrane module the water concentration is higher than the concentrating fluid fed to downstream one, the condensation load can be borne at the condensation temperatures corresponding to the then water partial pressure. Since a cold source, such as cooling water of a cooling tower, a water chiller, and a brine chiller, requires more power per cooling load as the temperature decreases, by using or more vacuum systems so as to use a higher condensation temperature for an upstream membrane module, the power load of the cold source can be reduced. Since the pressure at the permeated side of an upstream membrane module can be raised (lower degree of vacuum) compared to the case of a treatment with a single vacuum system, the pump capacity of the vacuum apparatus can be reduced, and therefore the power consumption of the pump can be reduced on top of the reduction of the power load of the cold source.

With respect to a water-alcohol separation system of an embodiment of the present invention, the separation system includes a separation membrane module, a vacuum system, a condenser, which is a heat exchanger, etc. Meanwhile, the separation membrane module includes a membrane, a container shell, a feed port of a concentrating fluid, an outflow port of a concentrated liquid, and an outflow port on the permeated side separated by the membrane. A separation membrane module is herein also referred to as a "membrane module unit".

The number of separation membrane modules provided in a water-alcohol separation system may be two or more, and may be appropriately decided corresponding to the concentration of a concentrating fluid, the target concentration of the concentrated liquid (alcohol concentration of the product), the throughput, etc. For example, when the alcohol concentration of the concentrating fluid to be fed to the water-alcohol separation system is 87 mass %, and the alcohol concentration of the concentrated liquid is 98.9 mass %, for the first membrane module unit, 10 membrane modules provided with 4000 cylindrical zeolite membranes with a diameter of approximately 12 mm and a length of approximately 1200 mm in a container shell with a diameter of 850 mm are connected in series, and the second membrane module unit, which dehydrates the concentrated liquid concentrated by the first membrane module unit, may have a form connecting 6 similar membrane modules in series.

The outflow port on the permeated side of the separation membrane module is connected with the vacuum system. The vacuum system includes a vacuum apparatus for depressurizing the permeated side of the separation membrane module, and an exhaust piping for evacuating the gas inside the space on the permeated side. The vacuum apparatus evacuates the gas on the permeated side of the membrane module to lower the pressure at the permeated side of the membrane module, and there is no particular restriction thereon, insofar as a desired degree of vacuum can be obtained. Specific examples thereof include a vacuum pump, such as a turbo molecular pump, and a dry pump.

The condenser is installed upstream of the vacuum apparatus for the sake of preventing the permeated component (vapor having permeated the membrane) from being sucked by a vacuum apparatus in the vacuum system by condensing the vapor that has passed through the membrane into a liquid. Examples of the cold source for the condenser include cooling water of a cooling tower, a water chiller, and a brine chiller. A coolant may be selected according to the cooling temperature for condensing the permeated component, and specific examples thereof include water; an organic brine containing methanol, ethanol, ethylene glycol, propylene glycol, or the like as a main component; a NaCl brine; and an ammonia coolant.

The number of vacuum systems included in a water-alcohol separation system in an embodiment of the present invention is 2 or more. As the number of vacuum systems increases, although the complexity of design, and the costs of vacuum apparatus tend to increase subject to the number of modules, or the throughput of the system, the energy consumption is curtailed so that the energy consumption as the whole system can be suppressed to achieve cost reduction. From the viewpoint of balance among cost, design, and energy suppression, the number of vacuum systems is preferably from 2 or more and 4 or less, and more preferably 2 or more and 3 or less.

In a water-alcohol separation system in an embodiment of the present invention, a mode in which the plurality of the independent vacuum systems comprise at least a first vacuum system and a second vacuum system, and the pressure $P_1$ at the vacuum side of a separation membrane module placed most downstream in a first membrane module unit depressurized by the first vacuum system is higher than the pressure $P_2$ at the vacuum side of a separation membrane module placed most downstream in a second membrane module unit depressurized by the second vacuum system, is also preferable from the viewpoint of energy efficiency. In this regard, the pressure $P_1$ at the vacuum side of a separation membrane module placed most downstream in the membrane module unit depressurized by the first vacuum system is the absolute pressure at the outflow port on the permeated side of a separation membrane module placed most downstream in the first membrane module unit depressurized by the first vacuum system, and the pressure $P_2$ at the second vacuum side of a separation membrane module placed most downstream in the second membrane module unit depressurized by the second vacuum system is the absolute pressure at the outflow port on the permeated side of a separation membrane module placed most downstream in the second membrane module unit depressurized by the second vacuum system.

In a water-alcohol separation system in an embodiment of the present invention, the pressure $P_1$ at the vacuum side of the membrane of a separation membrane module placed most downstream in the first vacuum system is usually 20 kPa (absolute pressure) or less, preferably 10 kPa (absolute pressure) or less, and more preferably 7 kPa or less. In other words, the first vacuum apparatus preferably produces a vacuum in the aforedescribed range on the permeated side of a separation membrane module placed most downstream in the first vacuum system.

In a water-alcohol separation system in an embodiment of the present invention, a mode, in which the plurality of the independent vacuum systems comprise at least a first vacuum system and a second vacuum system; the first vacuum system is provided with a first condenser, and the second vacuum system is provided with a second condenser; and the temperature $T_1$ of a coolant retained by the first condenser is higher than the temperature $T_2$ of a coolant retained by the second condenser, is preferable from the viewpoint of balance between energy efficiency and cost.

The condenser to be used according to the present invention may be a plurality of condensers connected in series, and in this case the temperatures of the coolants retained by the condensers may be different. In this regard, the expression of "the temperature of the coolant retained by the condenser" means the temperature of a coolant fed to the most downstream heat exchanger among a plurality of the heat exchangers connected in series.

In this case, the temperature $T_1$ is preferably 0° C. or more, more preferably 2° C. or more, further preferably 20° C. or more, and especially preferably 25° C. or more. Further, the temperature $T_1$ is preferably 35° C. or less, and more preferably 30° C. or less.

Meanwhile, the temperature $T_2$ is preferably 35° C. or less, more preferably 30° C. or less, further preferably 5° C. or less, and especially preferably 0° C. or less. Further, the temperature $T_2$ is preferably −10° C. or more, and more preferably −5° C. or more.

Further, when a third vacuum system is included as described below, the temperature $T_3$ of a coolant retained by the third condenser is preferably 30° C. or less, more preferably 5° C. or less, and further preferably 0° C. or less. Further, the temperature $T_3$ is preferably −10° C. or more, and more preferably −5° C. or more.

In a water-alcohol separation system in an embodiment of the present invention, a mode, in which the plurality of the independent vacuum systems comprise at least a first vacuum system and a second vacuum system; the first vacuum system is provided with a first condenser, and the second vacuum system is provided with a second condenser; and the temperature $T_1$ of a coolant retained by the first condenser is 20° C. or higher, and the temperature $T_2$ of a coolant retained by the second condenser is 35° C. or lower, is also preferable from the viewpoint of balance between energy efficiency and cost. In this embodiment, cooling water of a cooling tower is favorably used as the cold source for the first condenser, and a water chiller is favorably used as the cold source for the second condenser.

In a water-alcohol separation system in an embodiment of the present invention, a mode, in which the plurality of the independent vacuum systems comprise at least a first vacuum system and a second vacuum system; the first vacuum system is provided with a first condenser, and the second vacuum system is provided with a second condenser; and the temperature $T_1$ of a coolant retained by the first condenser is 0° C. or higher, and the temperature $T_2$ of a coolant retained by the second condenser is 5° C. or lower, is also preferable from the viewpoint of producing an alcohol of higher purity. A water chiller is favorably used as the cold source for the first condenser, and a brine chiller is favorably used as the cold source for the second condenser.

In a water-alcohol separation system in an embodiment of the present invention, a mode, in which the plurality of the independent vacuum systems comprise at least a first vacuum system, a second vacuum system, and a third vacuum system; the first vacuum system is provided with a first condenser, the second vacuum system is provided with a second condenser, and the third vacuum system is provided with a third condenser; and the temperature $T_1$ of a coolant retained by the first condenser is 20° C. or higher, the temperature $T_2$ of a coolant retained by the second condenser is 35° C. or lower, and the temperature $T_3$ of a coolant retained by the third condenser is 5° C. or lower, is also preferable from the viewpoint of producing an alcohol of higher purity.

In this embodiment, favorably cooling water of a cooling tower is used as the cold source for the first condenser, a cold-water chiller as the cold source for the second condenser, and a brine chiller as the cold source for the third condenser.

In a water-alcohol separation system in an embodiment of the present invention, the membrane of a separation membrane module is usually a separation membrane having a dehydration function, and examples thereof include a polymer membrane such as a polyimide membrane, and a zeolite membrane. Further, there is no particular restriction on the shape thereof, and it may be any of a flat, tubular, honeycomb, monolithic, or hollow fiber. As materials for a container shell, a feed port for a concentrating fluid, an outflow port for a concentrated liquid, and an outflow port on the permeated side separated by a membrane constituting a separation membrane module, publicly known materials may be utilized.

In a water-alcohol separation system in an embodiment of the present invention, since the degree of vacuum on the permeated side of an upstream membrane module can be made lower (higher pressure) compared to the case where a single vacuum system is operated, the permeation flux of water can be kept in a preferable range. The permeation flux of water of the most downstream membrane module is preferably 0.1 kg/(m²·h) or more, more preferably 2.0 kg/(m²·h) or more, and further preferably 5.0 kg/(m²·h) or more. In a case where the permeation flux of water is in the aforedescribed range, when a product is obtained directly from the water-alcohol separation system, the production efficiency can be enhanced, and when the flux is recycled from the water-alcohol separation system to the adsorption apparatus described below, the energy efficiency of the adsorption apparatus can be enhanced. When the value of the permeation flux is large, it is possible to design a smaller separation membrane area, and to downsize the apparatus, while keeping the desired concentration amount and concentration rate in a water-alcohol separation system.

As an example of a separation membrane, a zeolite membrane will be described in detail below.

As a zeolite membrane, it is preferable to use a porous support-zeolite membrane complex (hereinafter referred to as "zeolite membrane complex") formed on a porous support.

There is no particular restriction on the porous support, insofar as it has such a chemical stability so that it can tightly adsorb, or preferably crystallize, zeolite in a film form on the surface, and is porous. Among others, an inorganic porous support is preferable, and examples thereof include sintered ceramics, such as silica, α-alumina, γ-alumina, mullite, zirconia, titania, yttria, silicon nitride, and silicon carbide, sintered metals, such as iron, bronze, and stainless steel, glass, and molded carbon.

Among inorganic porous supports, a porous support containing a sintered body of a ceramic, the basic part or most part of which is a solid material composed of an inorganic non-metallic substance (ceramics support) is especially preferable, because the adhesion at the interface is strengthened by zeolitization of a part of the support during synthesis of a zeolite membrane.

Specific examples thereof include sintered ceramics (ceramic supports) containing silica, α-alumina, γ-alumina, mullite, zirconia, titania, yttria, silicon nitride, and silicon carbide, or the like. Among them, a porous support containing at least one of alumina, silica, and mullite is preferable, because zeolitization of a part of the porous support is easy so that the bond between the porous support and zeolitize becomes firm and a dense membrane with a high separation performance can be easily formed.

Since a zeolite membrane complex has a support, its mechanical strength is increased so that handling becomes easier allowing flexible design of a variety of apparatus. Further, in the case of an inorganic porous support, since it is composed of an inorganic substance, it is superior in heat resistance and chemical resistance.

There is no particular restriction on the shape of a porous support, insofar as a mixture of liquid or gas can be effectively separated. Specific examples thereof include a flat, tubular, honeycomb with a large number of cylindrical, columnar, or prismatic pores, or similar form, and any of these shapes may be used.

It is preferable that zeolite is crystallized on the surface of a porous support (hereinafter also referred to as "porous support surface").

Although there is no particular restriction on the average pore size at the porous support surface, it is preferable that the pore size is regulated usually at 0.02 μm or more, preferably 0.05 μm or more, further preferably 0.1 μm or more, and especially preferably 0.5 μm or more, and usually at 20 μm or less, preferably 10 μm or less, and more preferably 5 μm or less.

When the average pore size is too small, the permeated amount tends to decrease, and when it is too large, the strength of a support itself may become insufficient, and the percentage of pores in the support surface increases and a dense zeolite membrane may be hardly formed.

The average thickness of a porous support is usually 0.1 mm or more, preferably 0.3 mm or more, more preferably 0.5 mm or more, and especially preferably 0.7 mm or more; and usually 7 mm or less, preferably 5 mm or less, and more preferably 3 mm or less.

The support is used for endowing a zeolite membrane with favorable mechanical strength. Therefore, when the average thickness is too thin, a porous support-zeolite membrane complex cannot be strong enough, and the porous support-zeolite membrane complex is vulnerable to shocks or vibrations, which tends to cause problems in a practical use. When the average thickness of a support is too thick, the diffusion of a permeated substance tends to be poor, and the permeation flux tends to decrease.

When the porous support is a cylindrical tube, the outer diameter of the cylindrical tube is usually 3 mm or more, preferably 5.5 mm or more, more preferably 9.5 mm or more, and especially preferably 11 mm or more, and usually 51 mm or less, preferably 31 mm or less, more preferably 21 mm or less, further preferably 17 mm or less, and especially preferably 15 mm or less.

Although the support is used for endowing a zeolite membrane with favorable mechanical strength, in a case where the support is a cylindrical tube, when the outer diameter is too small, a porous support-zeolite membrane complex cannot be strong enough, and the porous support-zeolite membrane complex is vulnerable to shocks or vibrations, which tends to cause problems in a practical use. In a case where the support is a cylindrical tube, when the outer diameter is too large, the membrane area per volume decreases, and therefore the volume of membrane required for obtaining a necessary membrane area becomes so large, that a large installation space, or a large sized module tends to be required, which is economically disadvantageous.

Further, the surface of a porous support is preferably smooth, and the surface may be polished according to need with a file, or the like.

Incidentally, a porous support surface means, for example, a surface portion of an inorganic porous support, on which zeolite is crystallized. The surface may be any part of surface, or surfaces, irrespective of the respective shapes. For example, in the case of a support in a cylindrical tube form it may be the outer surface, or the inner surface, or both the outer surface and the inner surface, as the case may be.

Further, there is no particular restriction on the pore size of the porous support at a portion other than the porous support surface.

The porosity of the porous support is usually 20% or more, preferably 25% or more, and more preferably 30% or more, and usually 70% or less, preferably 60% or less, and more preferably 50% or less.

The porosity of the porous support has a strong influence on the permeation flow rate at the time of separation of a gas or a liquid. When the porosity is less than the aforedescribed lower limit, the diffusion of a permeated substance tends to be impeded, and when the porosity exceeds the aforedescribed upper limit, the strength of the porous support tends to be decreased.

The molar ratio $SiO_2/Al_2O_3$ of the main zeolite constituting a zeolite membrane is preferably 5 or more, more preferably 8 or more, further preferably 10 or more, and especially preferably 12 or more, and usually 2000 or less, preferably 1000 or less, more preferably 500 or less, further preferably 100 or less, especially preferably 20 or less, and most preferably 17 or less. When the molar ratio $SiO_2/Al_2O_3$ is less than the lower limit, the durability tends to decrease, and when it exceeds the upper limit, the hydrophobicity is too strong, so the permeation flux tends to decrease.

The molar ratio of $SiO_2/Al_2O_3$ in the present invention is a value determined by a scanning electron microscope-energy dispersive X-ray spectrometry method (SEM-EDX). In order to obtain information solely on a few micron-thick membrane, a measurement is performed usually with an X-ray at the accelerating voltage of 10 kV.

Although there is no particular restriction on the framework density of a main zeolite constituting a zeolite membrane, it is preferably 10.0 T/1000 Å or more, and more preferably 14.0 T/1000 Å or more, and preferably 18.0 T/1000 Å or less, more preferably 17.0 T/1000 Å or less, further preferably 16.0 T/1000 Å or less, and most preferably 15.0 T/1000 Å or less. The aforedescribed range is preferable from the viewpoint of durability.

A framework density means the number of T elements constituting the framework of a zeolite other than oxygen per 1000 $Å^3$ of the zeolite, and this value is determined by the structure of the zeolite. The relationship between the framework density and the structure of a zeolite is shown in ATLAS OF ZEOLITE FRAMEWORK TYPES, Fifth Revised Edition 2001 ELSEVIER.

A main zeolite constituting a zeolite membrane is usually a zeolite having a 6 to 12-membered oxygen ring structure, preferably a 6 to 10-membered oxygen ring structure, and more preferably an 8-membered oxygen ring.

In this case, the value n of a zeolite having an n-membered oxygen ring indicates the largest oxygen number among pores constituted with oxygen and T elements forming the zeolite framework. For example, when there are a pore with a 12-membered oxygen ring and a pore with an 8-membered oxygen ring as in a MOR type zeolite, it is regarded as a zeolite of a 12-membered oxygen ring.

Examples of a zeolite having an 6 to 10-membered oxygen ring structure include AEI, AEL, AFG, ANA, BRE, CAS, CDO, CHA, DAC, DDR, DOH, EAB, EPI, ESV, EUO, FAR, FRA, FER, GIS, GIU, GOO, HEU, ITE, ITH, KFI, LEV, LIO, LOS, LTA, LTN, MAR, MEP, MER, MEL, MFI, MFS, MON, MSO, MTF, MTN, MTT, MWW, NAT, NES, NON, PAU, PHI, RHO, RRO, RTE, RTH, RUT, SGT, SOD, STF, STI, STT, TER, TOL, TON, TSC, TUN, UFI, VNI, VSV, WEI, and YUG.

When the structure is larger than a 10-membered oxygen ring structure, the pore size becomes large, and for an organic substance having a small size, the separation performance is decreased, and the application thereof may be limited.

Among the above, preferable zeolite structures are AEI, CHA, KFI, LEV, LTA, PAU, RHO, RTH, and UFI; more preferable are CHA, LEV, LTA, and UFI; further preferable are CHA or LTA; and especially preferable is LTA.

Although there is no particular restriction on the thickness of a zeolite membrane, it is usually 0.1 μm or more, preferably 0.6 μm or more, more preferably 1.0 μm or more, further preferably 5 μm, and especially preferably 7 μm or more. Further, the thickness of a zeolite membrane is usually in a range of 100 μm or less, preferably 60 μm or less, more preferably 20 μm or less, and especially preferably 10 μm or less. When the membrane thickness is too large, the permeated amount tends to decrease, and when it is too small, the selectivity or the membrane strength tends to decrease.

Although there is no particular restriction on the particle diameter of a zeolite that forms a zeolite membrane, when it is too small, there is a tendency that the grain boundary becomes large to decrease the permeation selectivity, etc. Therefore, the diameter is usually 30 nm or more, preferably 50 nm or more, and more preferably 100 nm or more, and the upper limit is the membrane thickness or less. More preferably, the particle diameter of zeolite is the same as the membrane thickness. This is because, when the particle size of a zeolite is the same as the membrane thickness, the grain boundary of the zeolite becomes minimum. A zeolite membrane obtained by hydrothermal synthesis is preferable, because the particle diameter of the zeolite may become the same as the membrane thickness.

A zeolite membrane may be produced by a heretofore well-known hydrothermal synthesis method, or the like, and the zeolite membrane may be optionally subjected to a silylation treatment using a silylation agent.

In a water-alcohol separation system in an embodiment of the present invention, the above separation membrane module preferably includes an inorganic porous support-zeolite membrane complex provided with a zeolite membrane on the surface of an inorganic porous support.

2. Method for Separating Water and an Alcohol

A method for water-alcohol separation in an embodiment of the present invention can be suitably used in a separation step for producing an alcohol.

In the following, a fermentation step, in which an alcohol fermentation raw material is fermented to yield a water-alcohol mixture, a concentration step, in which the water-alcohol mixture is introduced into a distillation column and concentrated, and a separation step, in which the water-alcohol mixture (liquid and/or gas) that has undergone the concentration step is introduced into a membrane separation apparatus and the water and alcohol in the mixture (liquid and/or gas) are separated, generally included in a method for producing an alcohol, will be described.

Preferable examples of an alcohol to be produced include a lower alcohol produced industrially in a large scale, such as methanol, ethanol, and a mixture thereof.

The fermentation step is a step of performing alcohol fermentation on an alcohol fermentation raw material with microorganisms such as fermentation germ to yield a water-alcohol mixture by this alcohol fermentation.

There is no particular restriction on the fermentation germ, insofar as it is a microorganism that carries out alcohol fermentation utilizing at least one of glucose, and a dimer or multimer of glucose as a carbon source, and examples thereof include yeast and *Zymomonas*.

In this regard, there may be a pretreatment step, such as a grinding treatment or an enzyme treatment before supplying a raw material to the fermentation step.

The alcohol concentration of the water-alcohol mixture yielded in the fermentation step is usually 1 mass % or more, and 20 mass % or less, and the alcohol concentration is increased through the concentration step described later.

When the alcohol concentration of the water-alcohol mixture yielded in the fermentation step is low, the water-alcohol mixture may be fed to a preliminary distillation column such as a moromi column, etc. to increase the alcohol concentration prior to the concentration step. From the viewpoint of reducing energy consumption, it is preferable to increase the alcohol concentration in the preliminary distillation column usually to 30 mass % or more, preferably 35 mass % or more, more preferably 40 mass % or more, and further preferably 45 mass % or more. Although there is no particular restriction on the upper limit, it is usually less than 70 mass %, preferably 65 mass % or less, more preferably 60 mass % or less, and further preferably 55 mass % or less. When the alcohol concentration is in the above range, almost no reflux is required, and the amount of water to be evaporated is also small.

Also, if necessary, filtration, such as microfiltration, ultrafiltration, and nanofiltration, or a neutralization treatment may be performed singly or in a combination in order to remove an unnecessary substance, or a high molecular weight component in the solution.

In the present embodiment, the concentration step is a step of increasing the alcohol concentration in the water-alcohol mixture, in which the water-alcohol mixture yielded in the fermentation step is introduced into a distillation column to increase the alcohol concentration. A distillate distilled out from the distillation column, for example, the overhead product of the distillation column, has usually an alcohol concentration of 70 mass % or more, preferably 80 mass % or more, and more preferably 85 mass % or more, and usually 98 mass % or less, preferably 95 mass % or less, and more preferably 90 mass % or less. When the alcohol concentration is below the upper limit, the energy efficiency of the whole process tends to be improved due to reduction of the load on the distillation column. In addition, when the alcohol concentration is not less than the lower limit, the possibility of an increase in the equipment cost due to size increase in the adsorption equipment can be avoided, because the water concentration is not too high, and the filling amount of the adsorbent is not increased. Further, the regeneration frequency of the adsorbent in the adsorption apparatus can be suppressed, and the operating cost also tends to be suppressed.

The distillation column may be provided with a side stripper. When a side stripper is provided, the water-alcohol mixture can be withdrawn from one or several positions in the middle stage of the distillation column, and purified.

The separation step is a step of introducing the water-alcohol mixture that has undergone the concentration step into a water-alcohol separation system in the mixture.

The water-alcohol mixture that has undergone the concentration step may be introduced as it is into a separation apparatus, or alternatively the water-alcohol mixture that has undergone the concentration step may be introduced first into an adsorption apparatus, and then, after going through the adsorption step of removing the water in the mixture, introduced into a separation apparatus. In this regard, the water-alcohol mixture is a liquid and/or gas.

An adsorption column used in the adsorption step may be based on any of pressure swing adsorption (PSA), temperature swing adsorption (TSA), or pressure and temperature swing adsorption (PTSA) combining the two.

The PSA has a function of adsorbing water or the like with the adsorbent by raising the pressure, and desorbing water or the like from the adsorbent by lowering the pressure. On the other hand, TSA has a function of adsorbing water or the like with the adsorbent and desorbing water or the like from the adsorbent by supplying a heating gas (such as nitrogen) to raise the temperature.

PSA, TSA, and PTSA are widely used because of their relatively simple apparatus constitution, and as an adsorbent, "Molecular sieve" (trade name) which is a synthetic zeolite is favorably used because of its high dehydrating capacity.

Although there is no particular restriction on the alcohol concentration in the water-alcohol mixture introduced into the adsorption column, for example, it is usually 95 mass % or less, and preferably 92 mass % or less, and usually 50 mass % or more, preferably 70 mass % or more, more preferably 80 mass % or more, and further preferably 85 mass % or more. When the alcohol concentration is below the upper limit, the load on the distillation column, etc. in the previous step is small, and the overall energy efficiency tends to be improved. When the alcohol concentration is not less than the lower limit, the possibility of an increase in the equipment cost due to size increase in adsorption equipment can be avoided, because the water concentration is not too high, and the filling amount of the adsorbent is not increased. Further, the regeneration frequency of the adsorbent in the adsorption apparatus can be suppressed, and the operating cost also tends to be suppressed.

A method for water-alcohol separation in an embodiment of the present invention includes a step of introducing a water-alcohol mixture into a plurality of separation membrane modules connected in series, and a separation step of separating water and an alcohol by regulating a plurality of the separation membrane modules connected in series by a plurality of independent vacuum systems; wherein the separation step comprises a first separation step of separating the water-alcohol mixture by reducing the pressure of a membrane module by a vacuum system, and a second separation step of separating the water-alcohol mixture after the first separation step by reducing the pressure of a membrane module by another vacuum system; wherein the pressure of the first separation step, and the pressure of the second separation step are different. In this regard, the pressure of each separation step means the absolute pressure of an outflow port on the permeated side of the most downstream separation membrane module, which is regulated by a vacuum apparatus provided in the vacuum system.

It is also preferable that the method for water-alcohol separation in an embodiment of the present invention takes a mode, in which the plurality of the independent vacuum systems comprise a first vacuum system and a second vacuum system; a first separation step in which the first vacuum system depressurizes the permeated side of a first membrane module unit, and a second separation step in which the second vacuum system depressurizes the permeated side of a second membrane module unit, are included; and the pressure $P_1$ at a vacuum side of a separation membrane module placed most downstream in the first membrane module unit is higher than the pressure $P_2$ at a vacuum side of a separation membrane module placed most downstream in the second membrane module unit. The pressure $P_1$ on the vacuum side of the separation membrane module placed most downstream of the first membrane module unit is the absolute pressure of an outflow port on the permeated side of the separation membrane module placed most downstream of the first membrane module unit. The pressure $P_2$ on the vacuum side of the separation membrane module placed most downstream of the second membrane module unit is the absolute pressure of an outflow port on the permeated side of the separation membrane module placed most downstream of the second membrane module unit.

According to a method for water-alcohol separation in an embodiment of the present invention, by regulating the vacuum system of the separation step by a plurality of the independent vacuum systems, it becomes possible to depressurize the separation step to two or more different degrees of vacuum such that the permeated side pressure of an upstream membrane module is higher (lower degree of vacuum). Consequently, the pump capacity of the vacuum apparatus can be decreased, and the power consumption of the pump can be reduced, so that a high purity alcohol can be produced while attaining energy saving as the whole process.

In a method for water-alcohol separation in an embodiment of the present invention, the pressure $P_1$ at the vacuum side of the membrane of the separation membrane module placed most downstream of the membrane module unit depressurized by the first vacuum system is usually 20 kPa (absolute pressure) or less, preferably 10 kPa (absolute pressure) or less, and more preferably 7 kPa (absolute pressure) or less from the viewpoint of energy efficiency. In other words, it is preferable to regulate the first vacuum apparatus to produce a vacuum in the aforedescribed range at the permeated side of the separation membrane module placed most downstream of the membrane module unit depressurized by the first vacuum system.

In a method for water-alcohol separation in an embodiment of the present invention, a mode, in which a first condensation step of condensing a vapor that has passed through a membrane and is obtained in the first separation step, and a second condensing step of condensing a vapor that has passed through a membrane and is obtained in the second separation step; wherein the temperature $T_1$ of a coolant retained by a condenser in the first condensation step is higher than the temperature $T_2$ of a coolant retained by a condenser in the second condensation step, is also preferable.

By using a method for water-alcohol separation in an embodiment of the present invention in the separation step, the power load on the cold source can be reduced, so that a high purity alcohol can be produced while attaining energy saving as the whole process.

In a method for water-alcohol separation in an embodiment of the present invention, a mode, in which the plurality of the independent vacuum systems comprise at least a first vacuum system and a second vacuum system; the first vacuum system is provided with a first condenser, and the second vacuum system is provided with a second condenser; and the temperature of a coolant retained by the first condenser is 20° C. or higher, and the temperature of a coolant retained by the second condenser is 35° C. or lower, is also preferable from the viewpoint of energy efficiency. This mode is effective, when the concentration of the concentrated alcohol obtained in the separation step is 98% or more, and more preferably 99° or more.

In a method for water-alcohol separation in an embodiment of the present invention, a mode, in which the plurality of the independent vacuum systems comprise at least a first vacuum system and a second vacuum system; the first vacuum system is provided with a first condenser, and the second vacuum system is provided with a second condenser; and the temperature of a coolant retained by the first condenser is 0° C. or higher, and the temperature of a coolant retained by the second condenser is 5° C. or lower, is also preferable from the viewpoint of production of a higher purity alcohol. This mode is effective, when the concentration of the concentrated alcohol obtained in the separation step is 99% or more, and more preferably 99.8% or more.

In a method for water-alcohol separation in an embodiment of the present invention, a mode, in which the plurality of the independent vacuum systems comprise at least a first vacuum system, a second vacuum system, and a third vacuum system; the first vacuum system is provided with a first condenser, the second vacuum system is provided with a second condenser, and the third vacuum system is provided with a third condenser; and the temperature of a coolant retained by the first condenser is 20° C. or higher, the temperature of a coolant retained by the second condenser is 35° C. or lower, and the temperature of a coolant retained by the third condenser is 5° C. or lower is also preferable from the viewpoint of production of a higher purity alcohol. This mode is effective, when the concentration of the concentrated alcohol obtained in the separation step is 99% or more, and more preferably 99.8% or more.

In the separation step of the present embodiment, a pervaporation (PV) method, or a vapor-permeation (VP) method is adopted, however from the viewpoint of energy efficiency, it is more preferable to adopt a pervaporation (PV) method.

In the PV method, a liquid is brought into contact with a separation membrane and water is made to permeate it. That is, this system may be also called permeation vaporization or penetrative vaporization, and the mixture (feed liquid) is evaporated intercalating a separation membrane, through which only water is allowed to pass the membrane so that an alcohol is separated and concentrated. Since the feed liquid is cooled by the heat of vaporization, a heating means is needed to compensate for it.

In the case of the PV method, the temperature of the water-alcohol mixture (liquid and/or gas) fed to a separation membrane module is usually from 25 to 200° C., and preferably from 70 to 150° C. The operating pressure is usually from 0.1 to 1.5 MPa, and preferably from 0.2 to 0.8 MPa.

In the case of the VP method, the temperature of the superheated vapor of the alcohol-water mixture supplied to a separation membrane module is, putting the saturated vapor pressure temperature as T, usually from T+1 to T+100° C., and preferably from T+5 to T+30° C. The operating pressure (supply side pressure) is usually from 0.1 to 1.5 MPa, and preferably from 0.2 to 0.8 MPa.

An alcohol yielded after introduction to a membrane separation apparatus in the separation step can be used as a product when its concentration is sufficiently high. When the concentration is not high enough, it can be returned to the adsorption step, or the separation step.

Meanwhile, the permeation flux of water in a membrane separation apparatus is preferably 0.1 kg/(m²·h) or more, more preferably 2.0 kg/(m²·h) or more, and further preferably 5.0 kg/(m²·h) or more. When the permeation flux of water is in the aforedescribed range, in a case where the product is obtained directly from the membrane separation apparatus, the production efficiency can be enhanced, and in a case where the permeate is sent back from the membrane separation apparatus to the adsorption apparatus, the energy efficiency of the adsorption apparatus can be enhanced. Further, when the value of the permeation flux is large, it is possible to design a smaller separation membrane area, and to downsize the apparatus, while keeping the desired concentration amount and concentration rate in the membrane separation apparatus In a membrane separation apparatus, a water-alcohol separation system of an embodiment of the present invention may be used.

Specific embodiments will be described below with reference to drawings, provided that the present invention be not limited to the specific embodiments described below.

FIG. 1 shows a schematic diagram of a water-alcohol separation system including a first vacuum system and a second vacuum system of an embodiment of the present invention. A water-alcohol mixture as the concentrating fluid is charged into the system, and sent through the membrane modules M-1 to M-13, and the concentrated alcohol liquid is recovered as a product. The first vacuum system is connected with the membrane modules M-1 to M-7, and the second vacuum system is connected with the membrane modules M-8 to M-13. Each vacuum system is provided with a vacuum pump and depressurized by the same. Upstream of each vacuum pump there is a heat exchanger functioning as a condenser, and the condensed permeated component is held in a tank, and then discharged. Since the feed liquid is cooled by the heat of vaporization, a heating means is also provided to compensate for it.

Figure 2:
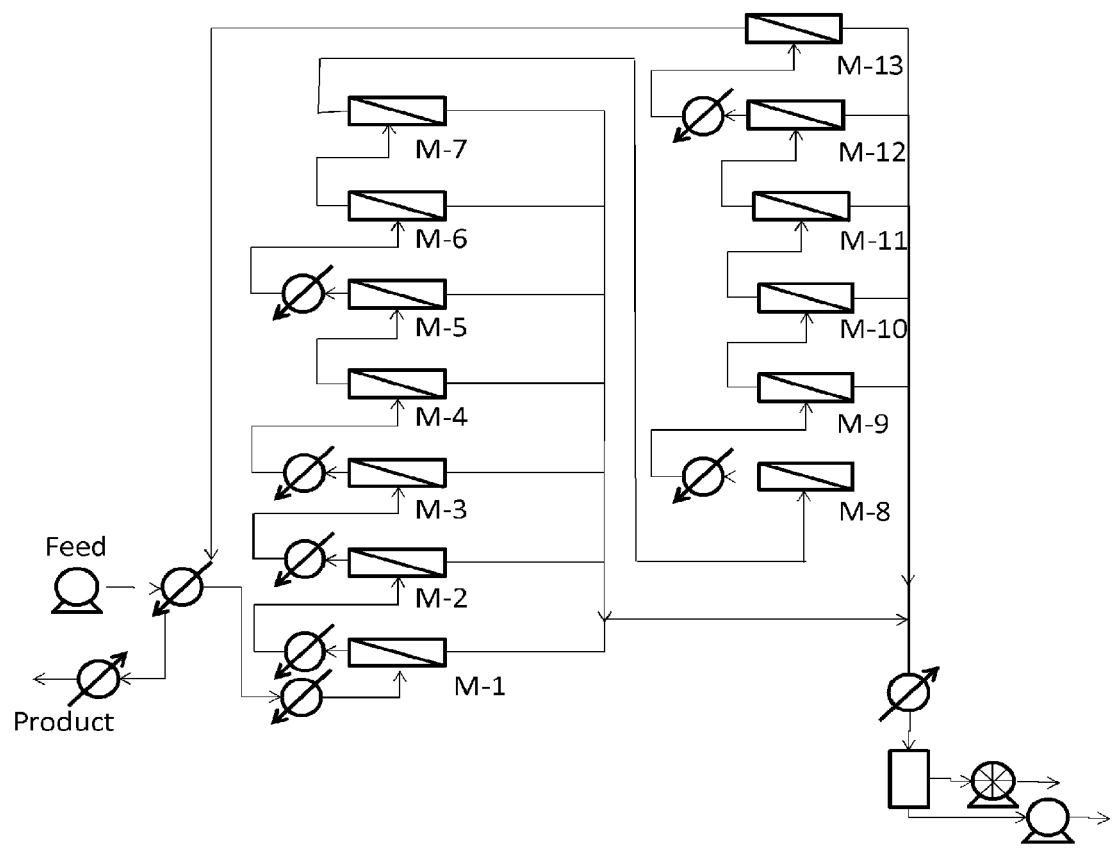
FIG. 2 shows a schematic diagram of a water-alcohol separation system, in which the vacuum system is constituted with a single system.

FIG. 2 shows a schematic diagram of a water-alcohol separation system, in which the vacuum system is constituted with a single system. A water-alcohol mixture as the concentrating fluid is charged into the system, and sent through the membrane modules M-1 to M-13, and the concentrated alcohol liquid is recovered as a product. All the membrane modules M-1 to M-13 are connected to one vacuum system, depressurized by one vacuum pump, and there is a heat exchanger functioning as a condenser upstream of the vacuum pump.

Figure 3:
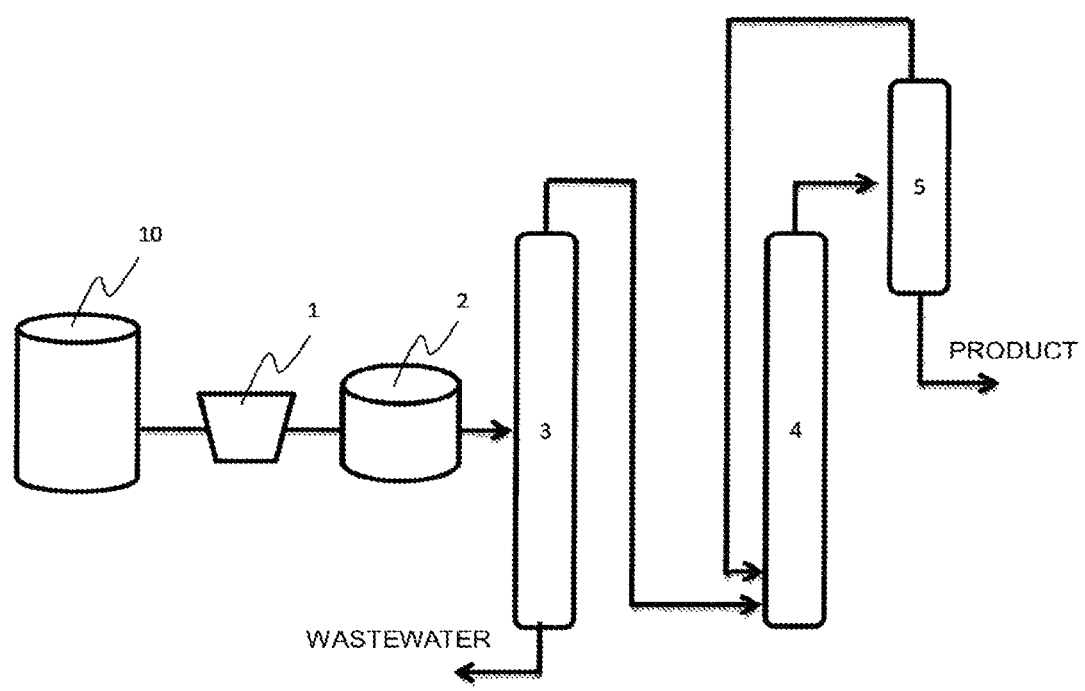
FIG. 3 is a flow diagram showing a method for producing an alcohol.

FIG. 3 is a flow diagram showing a method for producing an alcohol using a water-alcohol separation system of an embodiment of the present invention.

Examples of a raw material 10 to be fed to the process flow include a starch-rich raw material, and a fiber-rich raw material. The raw material 10 is introduced into a pulverizer 1 such as a mill and pulverized. The raw material is pulverized to a desired particle size by the pulverizer, and the particle size is also uniformized.

The raw material pulverized by the pulverizer 1 is fed to a fermenting vessel 2. The fermenting vessel 2 is provided with a yeast tank (not illustrated), and yeast is supplied from the yeast tank to the fermenting vessel 2 and alcohol fermentation is performed to convert the raw material into an alcohol. By alcohol fermentation, a water-alcohol mixture is yielded. Further, if necessary, the fermenting vessel 2 is provided with an enzyme tank (not illustrated), and an enzyme is supplied from the enzyme tank to the fermenting vessel 2, and the raw material is treated with the enzyme so as to improve the efficiency of the alcohol fermentation.

The water-alcohol mixture yielded in the fermenting vessel 2 is fed to a moromi column 3 for conducting predistillation to increase the alcohol concentration, and then the vapor from the moromi column 3 is fed to the distillation column 4, where the alcohol concentration is further increased. Then the vapor from the distillation column 4 is fed to the membrane separation apparatus 5. The wastewater of the moromi column 3 may be supplied to, for example, a feedstuff producing step (not illustrated).

The alcohol concentration is further increased in the membrane separation apparatus 5, and a high concentration alcohol is supplied as a product. When a water-alcohol separation system, or a method for water-alcohol separation according to one embodiment of the present invention is adopted in the membrane separation apparatus 5, the energy required for producing a unit volume of alcohol is reduced, and the production of a high purity alcohol production achieving energy saving as the whole process can be realized.

In the membrane separation apparatus 5, almost no alcohol is contained in the separated water, so that an alcohol product can be efficiently produced. Therefore it is possible to make the best use of such advantages as adequate purification capacity, and capability of performing pulverization, or enzyme treatment on a raw material.

EXAMPLES

A simulation performed as Examples by the present inventors will be described below.

The dehydration step in ethanol production using a separation membrane system in the membrane separation apparatus 5 was simulated in the process flow shown in FIG. 3.

Example 1

Figure 4:
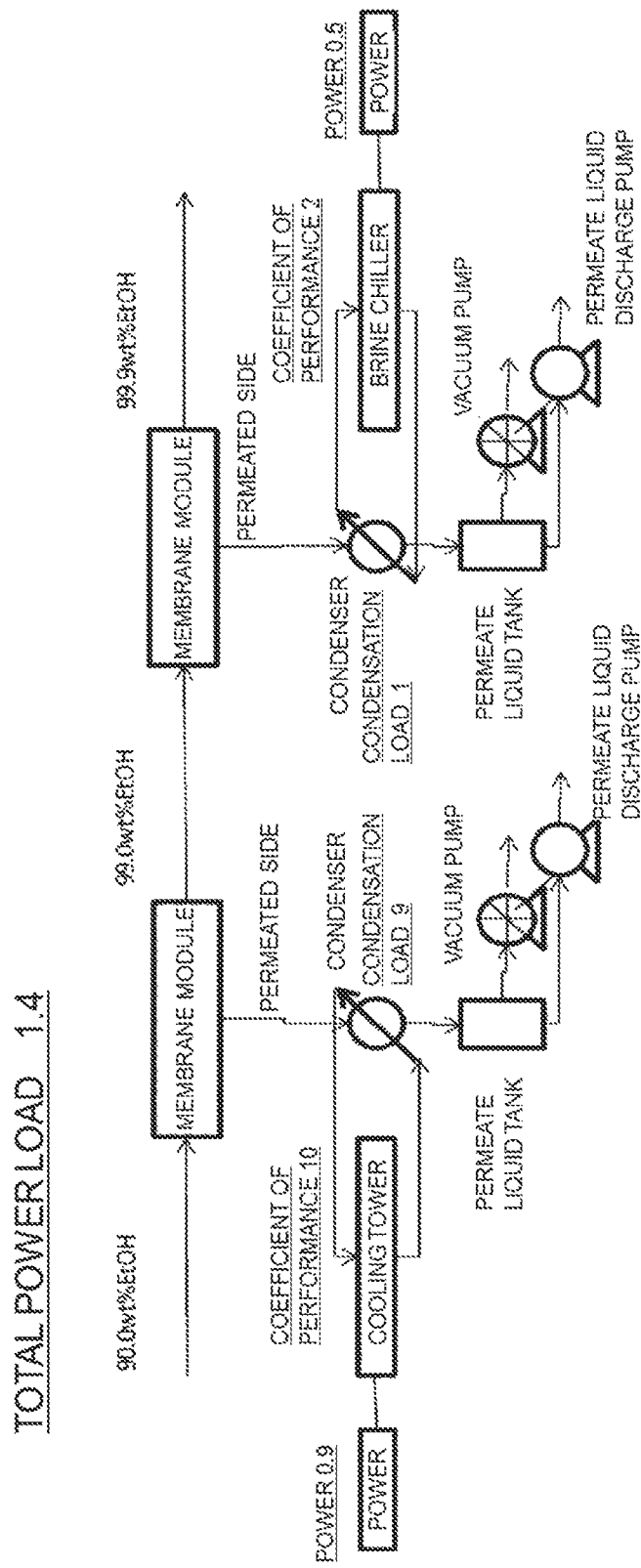
FIG. 4 is a simulation result showing a load on a water-alcohol separation system in Example 1.

The dehydration step in ethanol production was simulated according to the process flow shown in FIG. 4. The operating conditions were set as follows as premises for comparative process examination.

Raw material: Water-alcohol mixture containing 90.0 mass % of ethanol
Raw material feed rate: approximately 150 kg/hr
First vacuum system:
   Condenser (I): Cooled by cooling tower cold water (20° C. or higher) as a coolant.
Second vacuum system:
   Condenser (II): Cooled by a brine chiller (coolant: ammonia) to 5° C. or lower
Concentration of product ethanol: 99.9 mass %

The water-alcohol mixture containing 90.0 mass % of ethanol fed to the membrane module is concentrated to 99.0 mass % ethanol through the first membrane module unit, and then it is further dehydrated in a second membrane module unit to yield 99.9 mass %-ethanol. The membrane module unit is depressurized by a vacuum pump, and the permeated component of the first membrane module is condensed by the condenser (I) installed upstream of the vacuum pump, held in a permeate liquid tank, and then discharged. The permeated component of the second membrane module unit is condensed by the condenser (II) installed upstream of the vacuum pump, held in a permeate liquid tank, and then discharged. The results are shown in Table 1 and FIG. 4.

Comparative Example 1

Figure 5:
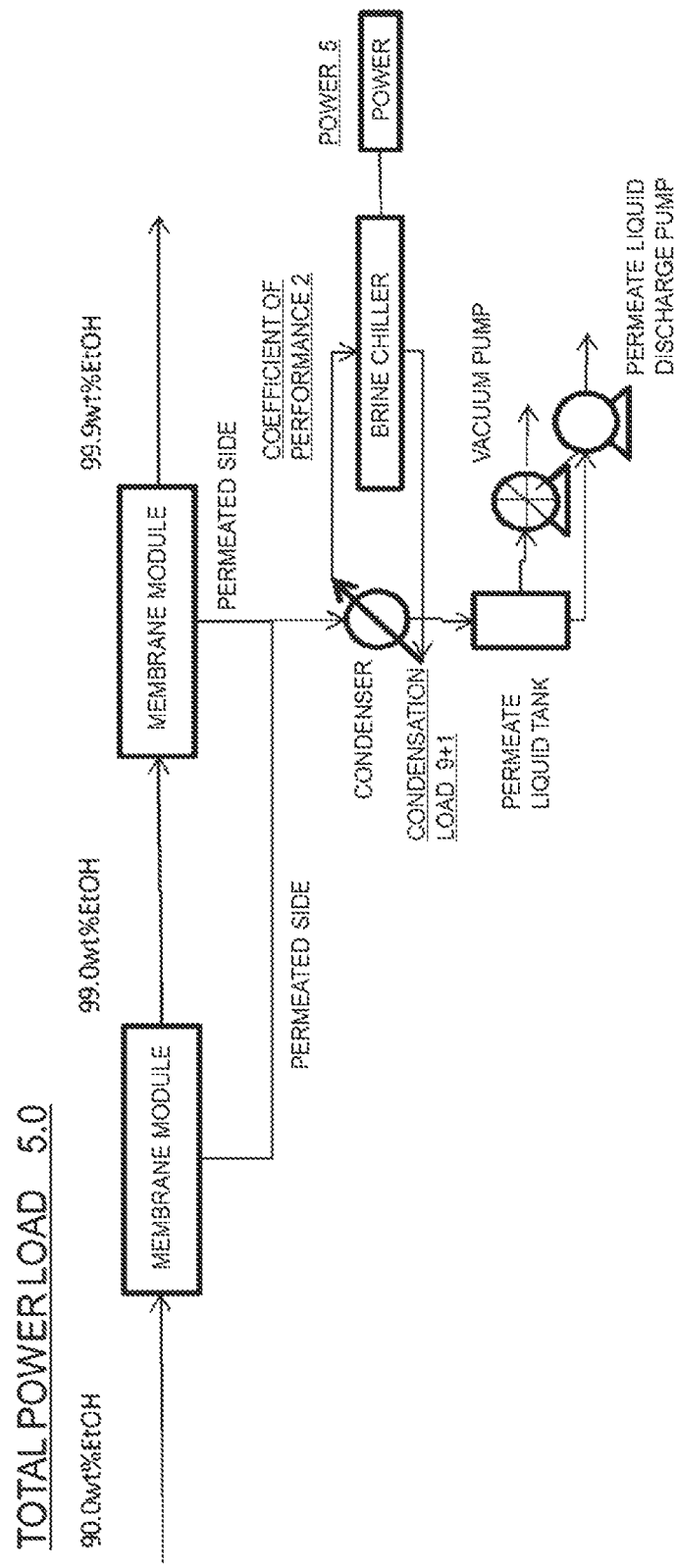
FIG. 5 is a simulation result showing a load on a water-alcohol separation system in Comparative Example 1.

The dehydration step in ethanol production was simulated according to the process flow shown in FIG. 5. The operating conditions were set as follows as premises for comparative process examination.

Raw material: Water-alcohol mixture containing 90.0 mass % of ethanol
Raw material feed rate: approximately 150 kg/hr
First vacuum system:
   Condenser (I): Cooled by a brine chiller (coolant: ammonia) to 5° C. or lower
Concentration of product ethanol: 99.9 mass %

The water-alcohol mixture containing 90.0 mass % of ethanol fed to the membrane module is dehydrated in a first membrane module unit to yield 99.9 mass %-ethanol. The membrane module unit is depressurized by a vacuum pump, and the permeated component of the first membrane module is condensed by the condenser (I) installed upstream of the vacuum pump, held in a permeate liquid tank, and then discharged. The results are shown in Table 1 and FIG. 5.

TABLE 1

|  | Example 1 | Comparative Example 1 |
|---|---|---|
| Condensation load (I) [kW] | 9 | 10 |
| Cooling tower Coefficient of performance | 10 | — |
| Cooling tower Power [kW] | 0.9 | — |
| Condensation load (II) [kW] | 1 | — |
| Brine chiller Coefficient of performance | 2 | 2 |
| Brine chiller Power [kW] | 0.5 | 5.0 |
| Total power load [kW] | 1.4 | 5.0 |

Coefficient of performance (COP) means (cooling capacity kW)/(input power kW) of each cooling apparatus.

From Table 1 as well as FIGS. 4 and 5, it has been made clear that the total load required for a water-alcohol separation system in Example is reduced by 72% compared to Comparative Example using a single vacuum system. From the above, it has been demonstrated by an Embodiment of the present invention, that a water-alcohol separation system, and a method for water-alcohol separation, by which a high purity alcohol can be produced while attaining energy saving as the whole process, can be provided.

Although the present invention has been described with reference to specific embodiments, each embodiment was presented as an example and does not limit the scope of the present invention. Each of the embodiments described herein can be variously modified without departing from the spirit of the invention, and can be combined with characteristics described by other embodiments so long as it can be enabled.

REFERENCE SIGNS LIST

1 Pulverizer
2 Fermenting vessel
3 Moromi column
4 Distillation column
5 Membrane separation apparatus
10 Cellulose-containing raw material

What is claimed is:

1. A water-alcohol separation system comprising:
a plurality of separation membrane modules connected in series,
a vacuum apparatus for reducing the pressure at a permeated side of a membrane of one or more of the separation membrane modules, and
a condenser for condensing a vapor that has passed through the membrane of the one or more of the separation membrane modules,
wherein all of the separation membrane modules are modules for a pervaporation (PV) method or all of the separation membrane modules are modules a vapor-permeation (VP) method,
wherein a plurality of independent vacuum systems which have at least two vacuum apparatuses and condensers reduce the pressure at the permeated side of the membrane of the one or more of the separation membrane modules,
wherein the plurality of the independent vacuum systems comprise at least a first vacuum system and a second vacuum system; the first vacuum system is provided with a first condenser, and the second vacuum system is provided with a second condenser; and a temperature $T_1$ of a coolant retained by the first condenser is higher than a temperature $T_2$ of a coolant retained by the second condenser,
wherein $T_1$ is 0° C. or more, and $T_2$ is 35° C. or less, and
wherein a pressure $P_1$ at a vacuum side of a membrane of a separation membrane module placed most downstream in a first membrane module unit depressurized by the first vacuum system is higher than a pressure $P_2$ at a vacuum side of a membrane of a separation membrane module placed most downstream in a second membrane module unit depressurized by the second vacuum system.

2. The water-alcohol separation system according to claim 1, wherein $T_1$ is 20° C. or higher.

3. The water-alcohol separation system according to claim 1, wherein $T_2$ is 5° C. or lower.

4. The water-alcohol separation system according to claim 1, wherein the plurality of the independent vacuum systems further comprises at least a third vacuum system;
wherein the third vacuum system is provided with a third condenser,
wherein a temperature of a coolant retained by the third condenser is 5° C. or lower, and
wherein $T_1$ is 20° C. or higher.

5. The water-alcohol separation system according to claim 1, wherein $P_1$ is 20 kPa (absolute pressure) or less.

6. The water-alcohol separation system according to claim 1, wherein a separation membrane module selected from the plurality of separation membrane modules is provided with an inorganic porous support-zeolite membrane complex comprising a zeolite membrane on the surface of an inorganic porous support.

7. A method for water-alcohol separation comprising:
a step of introducing a water-alcohol mixture into a plurality of separation membrane modules connected in series;
and a separation step of separating water and an alcohol from each other by controlling a plurality of the separation membrane modules connected in series by a plurality of independent vacuum systems;
wherein all of the separation membrane modules are modules for a pervaporation (PV) method or all of the separation membrane modules are modules for a vapor-permeation (VP) method, wherein the plurality of the independent vacuum systems comprise at least a first vacuum system and a second vacuum system; the first vacuum system is provided with a first condenser, and the second vacuum system is provided with a second condenser;

wherein the separation step comprises:

a first separation step of separating the water-alcohol mixture by reducing a pressure of a separation membrane module placed most downstream in a first membrane module unit by the first vacuum system to a pressure $P_1$, wherein the first vacuum system depressurizes a permeated side of the first membrane module unit, a first condensation step of condensing a vapor that has passed through a membrane of the separation membrane module placed most downstream in the first membrane module unit and is obtained from the first separation step;

a second separation step of separating the water-alcohol mixture after the first separation step by reducing a pressure of a separation membrane module placed most downstream in a second membrane module unit by the second vacuum system to a pressure $P_2$, wherein the second vacuum system depressurizes a permeated side of the second membrane module unit;

a second condensation step of condensing a vapor that has passed through a membrane of the separation membrane module placed most downstream in the second membrane module unit and is obtained from the second separation step;

wherein $P_1$ is higher than $P_2$;

wherein a temperature $T_1$ of a coolant retained by the first condenser is higher than a temperature $T_2$ of a coolant retained by the second condenser, and wherein $T_1$ is 0° C. or more, and $T_2$ is 35° C. or less.

8. The method for water-alcohol separation according to claim 7, wherein $T_1$ is 20° C. or higher.

9. The method for water-alcohol separation according to claim 7, wherein $T_2$ is 5° C. or lower.

10. The method for water-alcohol separation according to claim 7, wherein the plurality of the independent vacuum systems further comprises a third vacuum system provided with a third condenser; and wherein a temperature of a coolant retained by the third condenser is 5° C. or lower, and wherein $T_1$ is 20° C. or higher.

11. The method for water-alcohol separation according to claim 7, wherein $P_1$ is 20 kPa or less.

12. The method for water-alcohol separation according to claim 7, wherein a separation membrane module selected from the plurality of separation membrane modules is provided with an inorganic porous support-zeolite membrane complex comprising a zeolite membrane on the surface of an inorganic porous support.

* * * * *